(12) United States Patent
Hung

(10) Patent No.: US 7,204,809 B2
(45) Date of Patent: Apr. 17, 2007

(54) PRESSURIZING APPARATUS AND METHOD FOR THE SAME

(75) Inventor: Ching-Hsi Hung, Taipei (TW)

(73) Assignee: Rossmax International Ltd., Taipei (TW)

( * ) Notice: Subject to any disclaimer, the term of this patent is extended or adjusted under 35 U.S.C. 154(b) by 71 days.

(21) Appl. No.: 11/195,622

(22) Filed: Aug. 3, 2005

(65) Prior Publication Data

US 2007/0032730 A1   Feb. 8, 2007

(51) Int. Cl.
*A61B 5/00* (2006.01)
(52) U.S. Cl. .................. 600/494; 600/490; 600/496
(58) Field of Classification Search ................... None
See application file for complete search history.

(56) References Cited

U.S. PATENT DOCUMENTS 4,566,462 A * 1/1986 Janssen ..................... 600/490
4,669,485 A * 6/1987 Russell ...................... 600/492
4,969,466 A * 11/1990 Brooks ....................... 600/494
5,135,003 A * 8/1992 Souma ....................... 600/493
5,240,008 A * 8/1993 Newell ....................... 600/498
5,427,109 A * 6/1995 Frankenreiter ............. 600/493

FOREIGN PATENT DOCUMENTS

JP        2-234740       9/1990

* cited by examiner

*Primary Examiner*—Robert L. Nasser

(57) ABSTRACT

A pressurizing apparatus and method for adjusting an optimal pressurizing rate according to a cuff of various lengths. The pressurizing method measures the pressure values at two reference points and time duration to calculate a pressurizing rate. A control adjustment routine to control an adjustment of the pressurizing rate is decided according the calculated pressurizing rate and at least one control condition. The pump is pressurized according to the adjustment of the pressurizing rate. A diastolic pressure value is measured and the pressurizing of the pump is kept to measure a systolic pressure value. Afterward, the pressurizing is stopped to prevent uncomfortable feeling of user caused by rapidly pressurizing and de-pressurizing process.

6 Claims, 4 Drawing Sheets

PRESSURIZING APPARATUS AND METHOD FOR THE SAME

BACKGROUND OF THE INVENTION

1. Field of the Invention

The present invention relates to a smart pressurizing apparatus and a smart pressurizing method, more particularly to a smart pressurizing apparatus and a smart pressurizing method, which adjust an optimal pressurizing rate according to various cuff lengths, thus providing comfortable measurement for user.

2. Description of Related Art

The present electronic sphygmomanometer generally uses a pouch connected to a cuff thereof to pump the cuff up. When the electronic sphygmomanometer is in operation, a CPU in the electronic sphygmomanometer controls a pressurizing pump to pump the cuff with air in the pouch. Certain information, like systolic pressure (high pressure), diastolic pressure (low pressure), and pulse pressure signal can be measured with the electronic sphygmomanometer.

According to the regulation of EN1060-3 Clause 4/AAMI SP 10 Clause 4.6.1.1, the width of the cuff should be 40% of user limb and the length of the cuff should be 80–100% of the user limb. The cuff and pouch of wrong sizes will influence the accuracy of measurement.

Therefore, the conventional electronic sphygmomanometer uses the CPU to send on/off signals to control the pressurizing pump. However, the conventional electronic sphygmomanometer uses similar procedures for measurement, namely fast pressurize the cuff and then release the pressure of the cuff to measure systolic pressure value (high pressure) and diastolic pressure value (low pressure). The similar procedures are applied for users of different conditions, including normal people, hypertension people, and hypotension people. The electronic sphygmomanometer should constantly supply pressure to the cuff to precisely measure the systolic pressure value. If the pressure is not enough, the pressurizing step should be conducted again. It is inconvenience to user and some user may have blood stasis problem.

Japanese laid-open No. 2-234740 discloses an electronic sphygmomanometer, which uses sensor to control the pressurizing pump with reference to the specific systolic pressure value and diastolic pressure value of user. More particularly, the proposed electronic sphygmomanometer uses a sensor to measure the diastolic pressure value of user after a fast pressurizing step and then the proposed electronic sphygmomanometer switches to a slowly pressurizing step to measure the systolic pressure value and then ceases pressurizing step.

SUMMARY OF THE INVENTION

The present invention is intended to provide a smart pressurizing apparatus and a smart pressurizing method, which adjust an optimal pressurizing rate according to various cuff lengths, thus providing comfortable measurement for user.

Accordingly, the present invention provides a smart pressurizing apparatus and method adjusting an optimal pressurizing rate according to cuff of various lengths. The smart pressurizing method measures the pressure values at two reference points and time duration to calculate a pressurizing rate. A control adjustment routine to control an adjustment of the pressurizing rate is decided according to the calculated pressurizing rate and at least one control condition. The pump is pressurized according to the adjustment of the pressurizing rate. A diastolic pressure value is measured and the pressurizing of the pump is kept to measure a systolic pressure value. Afterward, the pressurizing is stopped to prevent uncomfortable feeling of user caused by rapidly pressurizing and de-pressurizing process.

BRIEF DESCRIPTION OF DRAWING

The features of the invention believed to be novel are set forth with particularity in the appended claims. The invention itself however may be best understood by reference to the following detailed description of the invention, which describes certain exemplary embodiments of the invention, taken in conjunction with the accompanying drawings in which:

DETAILED DESCRIPTION OF THE INVENTION

Figure 1:
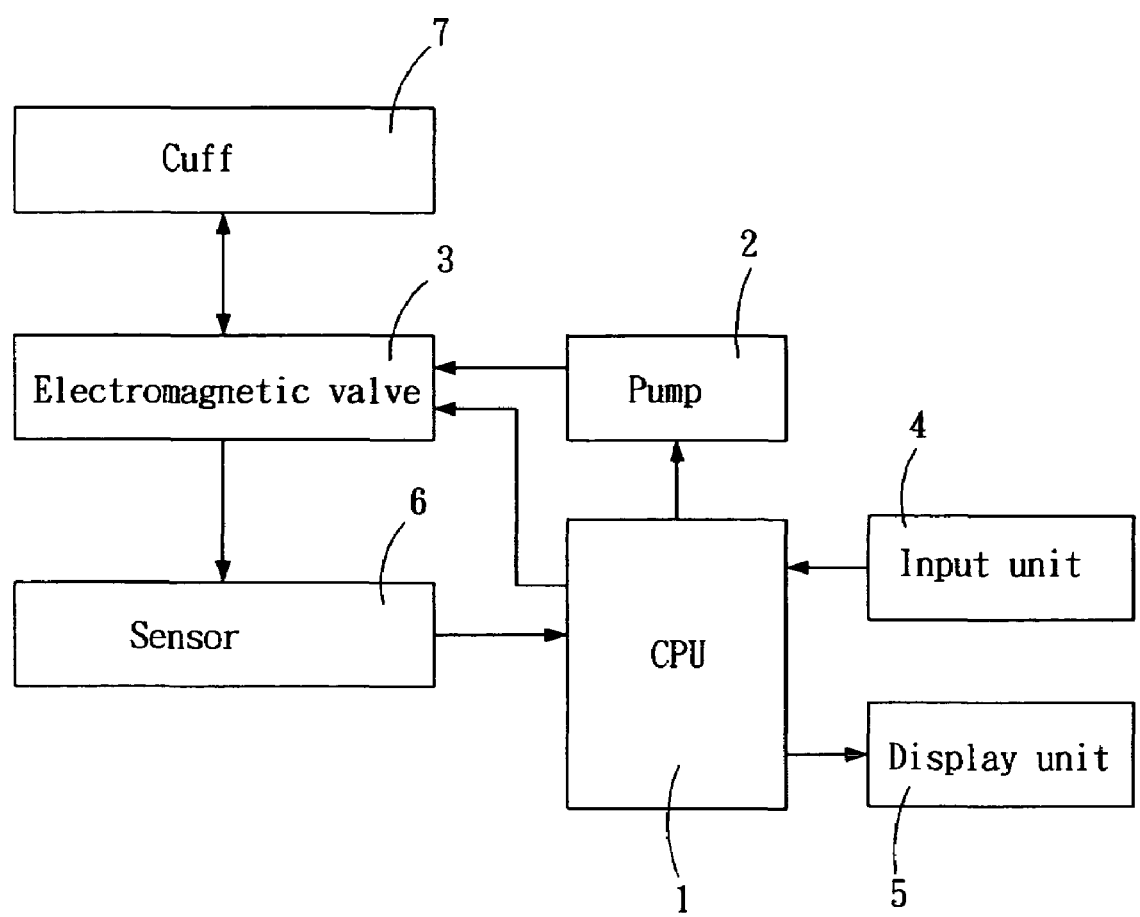
FIG. 1 shows a schematic diagram of a smart pressurizing apparatus of the present invention.
Figure 2:
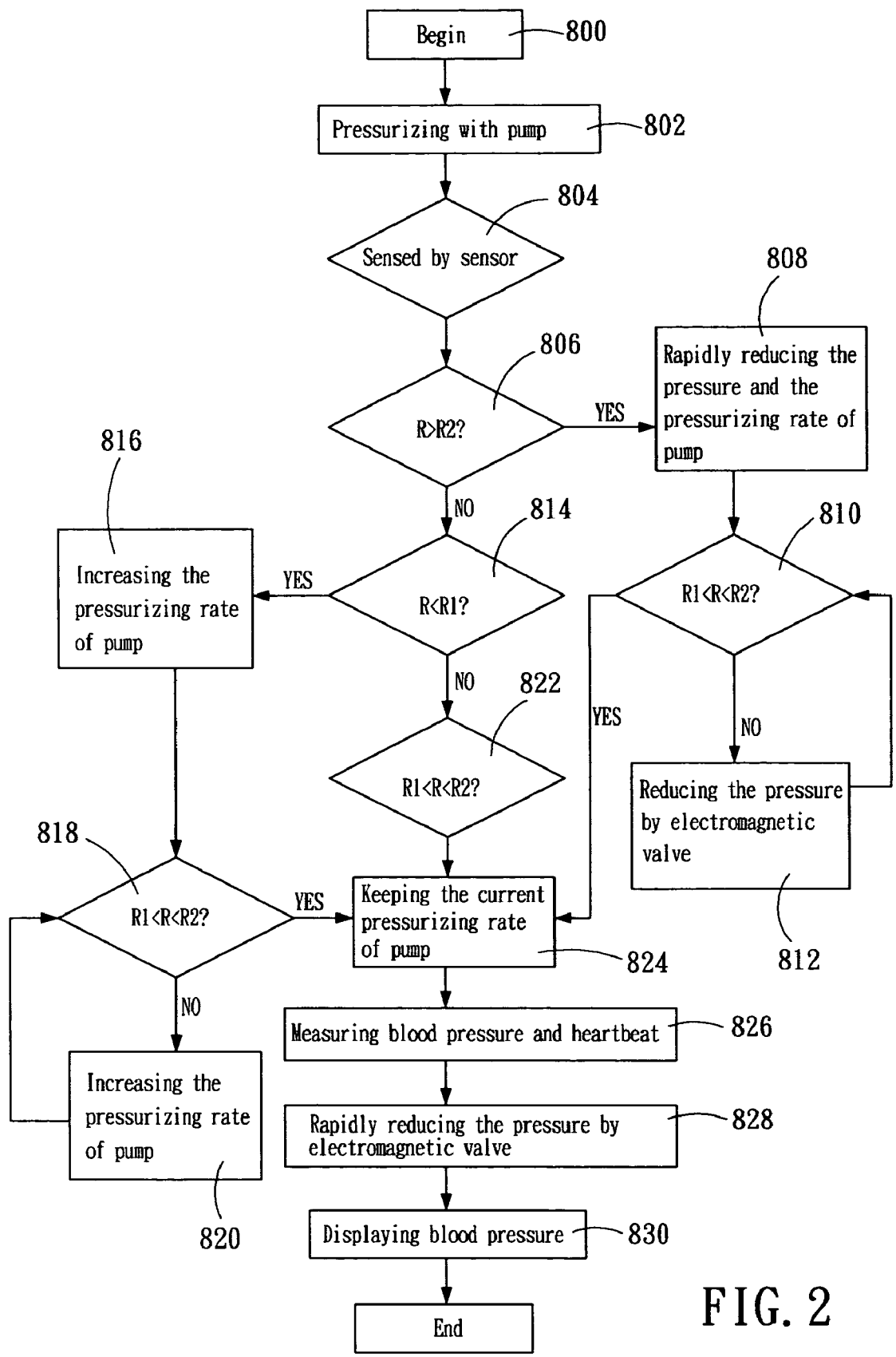
FIG. 2 shows the flowchart for operating the smart pressurizing apparatus of the present invention.

FIG. 1 shows a schematic diagram of a smart pressurizing apparatus of the present invention. As shown in this figure, the smart pressurizing apparatus of the present invention comprises a CPU 1, a pump 2 electrically connected to the CPU 1, an electromagnetic valve 3, an input unit 4 and a display unit 5, and above-mentioned components are assembled in a main body (not shown) of an electronic sphygmomanometer. The electromagnetic valve 3 is connected to a cuff 7 external to the electronic sphygmomanometer. Moreover, a sensor 6 is electrically connected to the CPU 1 and the electromagnetic valve 3 to sense a pressurizing state in the cuff 7 for pouches of different standards. The sensed result is sent to the CPU 1 for further processing to control a pressurizing rate of the pump 2 to provide a comfortable measurement for user.

During a first pressurizing procedure of the pump 2, the sensor 6 will measure the pressure value at a first checkpoint and a second checkpoint. The measurements at the first checkpoint and the second checkpoint will be sent to the CPU 1 for calculating control parameters and calculation parameters, those parameters determine a controlled pressurizing way and a pressurizing speed. The CPU 1 comprises a program to calculate a pressurizing rate at initial stage and compares the pressurizing rate with a default value to adjust later pressurizing rate and pressurizing way. For example, the later pressurizing way can be one of maintaining a feasible pressurizing rate, rapidly de-pressurizing to a preset value and then keeping a preferable pressurizing rate, increasing pressurizing rate and then switching to a feasible pressurizing rate. Therefore, the information of systolic pressure value, diastolic pressure value and heartbeat rate can be measured and the measured result is shown on the display unit 5.

Meanwhile, the pump 2 will cease pressurizing after the systolic pressure value is measured. Afterward, the pressure inside the cuff is decreased by operating the electromagnetic valve 3 to prevent uncomfortable feeling of user caused by rapid pressurizing step and to reduce measurement time.

With reference to FIGS. 2 to 5, in the present invention, the pressures at the first checkpoint and the second checkpoint during the pressurizing step are measured and then sent to the CPU 1 for parameter calculation and control adjustment.

The pressurizing rate of pump can be calculated as followings:

$$R=(X-Y)/T$$

where R is pressurizing rate of pump;

T is a pressurizing time between the first checkpoint and the second checkpoint (T=t2−t1);

X is a preset pressure value for the second checkpoint;

Y is a preset pressure value for the first checkpoint, wherein

X>Y, namely, the preset pressure value for the second checkpoint should be larger than the preset pressure value for the first checkpoint t1 is the time for pressurizing to the preset pressure value Y from the initial pressure;

t2 is the time for pressurizing to the preset pressure value X from the initial pressure;

R1 is the first control condition for the pressurizing rate of pump;

R2 is the second control condition for the pressurizing rate of pump, wherein

R2>R1, namely, the pressurizing rate of the second control condition is larger than the pressurizing rate of the first control condition.

The program in the CPU 1 comprises at least one control condition value and a control adjustment way corresponding to the control condition value. The control adjustment way includes following criterions.

Figure 3:
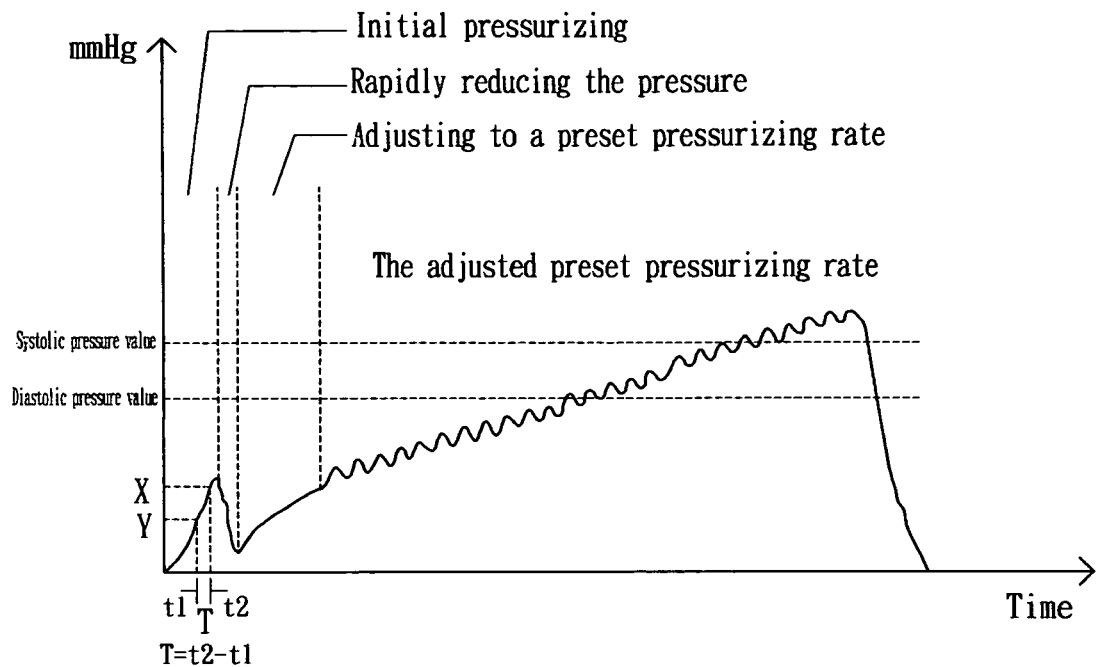
FIG. 3 shows a control adjustment routine for a specific control condition.

(1) When R>R2, the pressure is rapidly reduced and then the pump is adjusted to a preset pressurizing rate, as shown in FIG. 3.

Figure 4:
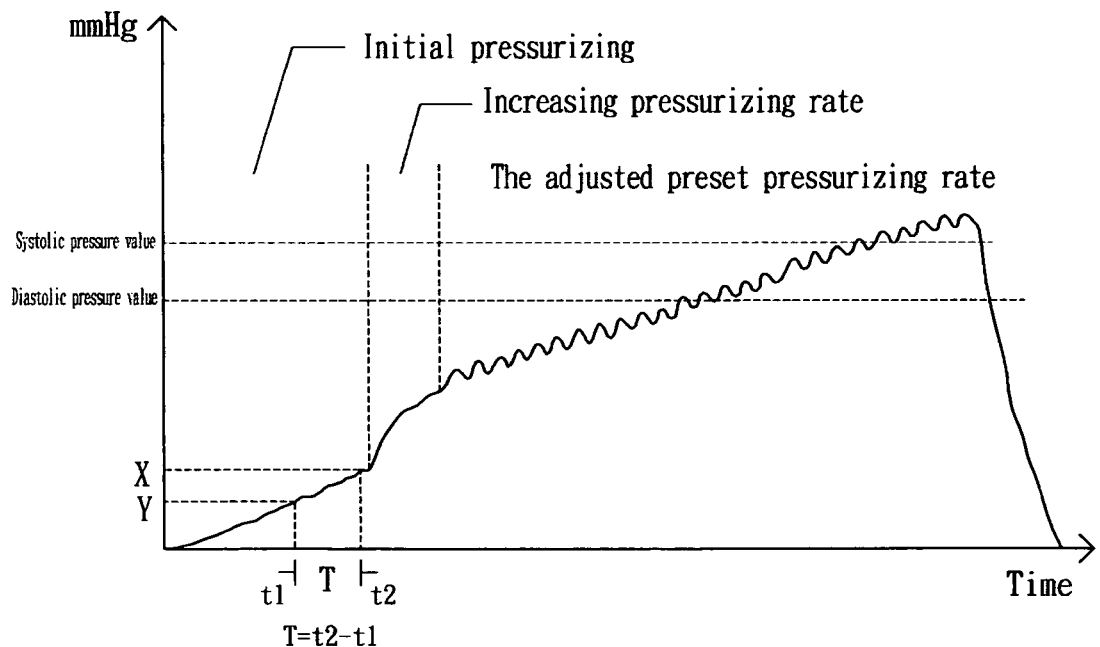
FIG. 4 shows a control adjustment routine for another specific control condition.

(2) When R<R1, the pressurizing rate of the pump is increased to the preset pressurizing rate and then keeps operation at the preset pressurizing rate, as shown in FIG. 4

Figure 5:
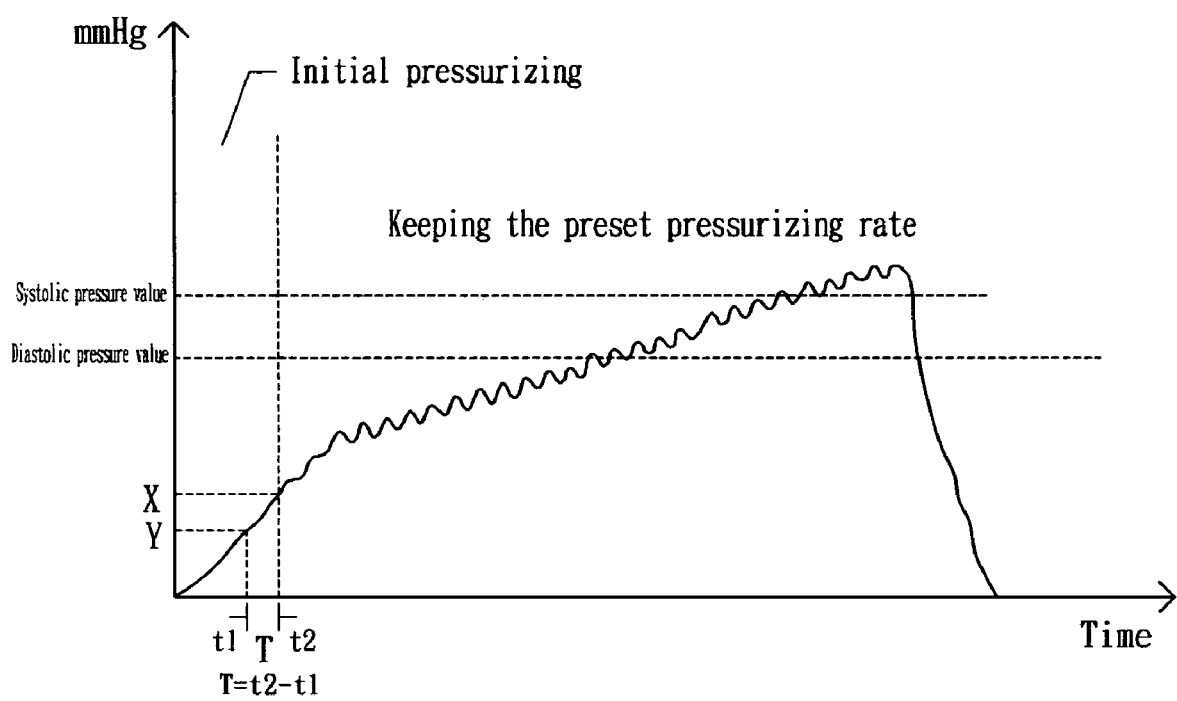
FIG. 5 shows a control adjustment routine for still another specific control condition.

(3) When R1<R<R2, the pump is kept to current pressurizing rate, as shown in FIG. 5.

In above description, the control condition value R is the pressurizing rate R with the range R1<R<R2.

The CPU 1 is electrically connected to the pump 2 and has operation steps as following. The CPU is started in step 800. In step 802, the CPU 1 controls the pump 2 to perform a first pressurizing stage.

The sensor 6 measures the pressure at the first checkpoint and the second checkpoint, respectively in step 804 and sends the measurement result to the CPU 1 to calculate the pressurizing rate in the first pressurizing stage.

Afterward, the control adjustment routine is performed in steps 806–810, wherein the pressurizing rate in the first pressurizing stage is used to determine the pressurizing rate in the second pressurizing stage.

Step 806 judges whether the measured pressurizing rate in the first pressurizing stage is larger than R2. If true, the CPU 1 activates the electromagnetic valve 3 to rapidly reduce pressure in step 808. Step 810 judges whether the measured pressurizing rate is within R1 and R2, namely, R1<R<R2. If false, step 812 is performed to still rapidly reduce pressure. If the measured pressurizing rate is within R1 and R2, then the current pressurizing rate R is used for pressurizing the cuff 7 in step 824. Afterward, the systolic pressure value, diastolic pressure value and heartbeat rate are measured in step 826. Afterward, the pressure is rapidly reduced using the electromagnetic valve 3 in step 828 and the measured blood pressures are displayed in the display unit 5 in step 830.

If in step 806 the measured pressurizing rate R in the first pressurizing stage is not larger than R2, then step 814 judges whether the measured pressurizing rate R is smaller than R1. If true, the pressurizing rate is increased in step 816 and then step 818 judges whether the measured pressurizing rate is within R1 and R2, namely, R1<R<R2. If false, step 822 is performed to still increase pressure. If the measured pressurizing rate is within R1 and R2, then the current pressurizing rate R is used for pressurizing the cuff 7 in step 824. Afterward, the systolic pressure value, diastolic pressure value and heartbeat rate are measured in step 826. Afterward, the pressure is rapidly reduced using the electromagnetic valve 3 in step 828 and the measured blood pressures are displayed in the display unit 5 in step 830.

If in step 814 the measured pressurizing rate R is not smaller than R1, then the pressurizing rate R is used for pressurizing the cuff 7 in step 824. Afterward, the systolic pressure value, diastolic pressure value and heartbeat rate are measured in step 826. Afterward, the pressure is rapidly reduced using the electromagnetic valve 3 in step 828 and the measured blood pressures are displayed in the display unit 5 in step 830.

Although the present invention has been described with reference to the preferred embodiment thereof, it will be understood that the invention is not limited to the details thereof. Various substitutions and modifications have suggested in the foregoing description, and other will occur to those of ordinary skill in the art. Therefore, all such substitutions and modifications are intended to be embraced within the scope of the invention as defined in the appended claims.

What is claimed is:

1. A pressurizing method for adjusting to an optimal pressurizing rate according to a cuff of various lengths, the method comprising the steps of:

starting a pump for a pressurizing rate at a first stage and obtaining a measured pressurizing rate at the first stage by measuring pressures at two checkpoints;

performing a control adjustment routine to control an adjustment of the pressurizing rate according the measured pressurizing rate, when the measured pressurizing rate R is larger than a second control condition R2, rapidly reducing the pressurizing rate to a preset value and then keeping pressurizing rate at the preset value, when the measured pressurizing rate R is smaller than a first control condition R1, increasing the pressurizing rate to the preset value and then keeping pressurizing rate at the preset value, when the measured pressurizing rate R is within the first control condition R1 and the second control condition R2, keeping the pump to operate at the measured pressurizing rate R;

pressurizing the pump according to the adjustment of the pressurizing rate, measuring a diastolic pressure value, keeping the pressurizing of the pump and then measuring a systolic pressure value and then stopping the pressurizing.

2. The pressurizing method as in claim 1, wherein the two checkpoints comprise a first checkpoint and a second checkpoint in the first stage to obtain a measured pressurizing rate.

3. The pressurizing method as in claim 1, further comprising the step of providing at least one control condition to perform the control adjustment routine with reference to the measured pressurizing rate.

4. The pressurizing method as in claim 1, wherein the first stage is a pressurizing step.

5. The pressurizing method as in claim 1, wherein the measured pressurizing rate is a difference of pressures measured in the two checkpoints divided by a time difference between the two checkpoints.

6. The pressurizing method as in claim 1, wherein the preset value is larger than the first control condition R1 and smaller than the second control condition R2.

* * * * *